(12) United States Patent
Harutyunyan et al.

(10) Patent No.: US 10,514,357 B2
(45) Date of Patent: Dec. 24, 2019

(54) CHEMICAL SENSOR BASED ON LAYERED NANORIBBONS

(71) Applicant: HONDA MOTOR CO., LTD., Minato-ku, Tokyo (JP)

(72) Inventors: Avetik Harutyunyan, Columbus, OH (US); Gugang Chen, Powell, OH (US)

(73) Assignee: HONDA MOTOR CO., LTD., Tokyo (JP)

(*) Notice: Subject to any disclaimer, the term of this patent is extended or adjusted under 35 U.S.C. 154(b) by 32 days.

(21) Appl. No.: 15/453,324

(22) Filed: Mar. 8, 2017

(65) Prior Publication Data

US 2017/0276641 A1 Sep. 28, 2017

Related U.S. Application Data

(60) Provisional application No. 62/313,526, filed on Mar. 25, 2016.

(51) Int. Cl.
| | |
|---|---|
| *G01N 27/414* | (2006.01) |
| *H01L 29/24* | (2006.01) |
| *H01L 21/02* | (2006.01) |
| *H01L 21/027* | (2006.01) |
| *H01L 21/04* | (2006.01) |
| *H01L 21/467* | (2006.01) |
| *H01L 29/16* | (2006.01) |

(52) U.S. Cl.
CPC ..... *G01N 27/4146* (2013.01); *H01L 21/0273* (2013.01); *H01L 21/02527* (2013.01); *H01L 21/02568* (2013.01); *H01L 21/042* (2013.01); *H01L 21/467* (2013.01); *H01L 29/1606* (2013.01); *H01L 29/24* (2013.01)

(58) Field of Classification Search
CPC ... G01N 27/4146; H01L 29/24; H01L 21/042; H01L 21/0273; H01L 29/1606; H01L 21/467; H01L 21/02568; H01L 21/02527
See application file for complete search history.

(56) References Cited

U.S. PATENT DOCUMENTS

| | | | | |
|---|---|---|---|---|
| 7,301,199 B2 * | 11/2007 | Lieber | .................. | B82Y 10/00 257/327 |
| 8,981,345 B2 | 3/2015 | Yu et al. | | |
| 2007/0275230 A1 * | 11/2007 | Murphy | ................. | C23C 24/08 428/323 |
| 2008/0030352 A1 | 2/2008 | Shaw | | |
| 2010/0224998 A1 | 9/2010 | Duvall et al. | | |

(Continued)

FOREIGN PATENT DOCUMENTS

| | | |
|---|---|---|
| CN | 104538449 A | 4/2015 |
| JP | 2013-012611 A | 1/2013 |

OTHER PUBLICATIONS

Akbari, et. al., "The effect of concentration on gas sensor model based on graphene nanoribbon," Neural Computing & Applications, vol. 24, (1), pp. 143-146, 2014.

(Continued)

*Primary Examiner* — Akm Zakaria
(74) *Attorney, Agent, or Firm* — Arent Fox LLP

(57) ABSTRACT

A chemical sensor is described having a substrate comprising a plurality of nanoribbons of an active layered nanomaterial, and a substance detection component for measuring a change in electrical or physical properties of at least a portion of the plurality of nanoribbons when in contact with a substance.

19 Claims, 5 Drawing Sheets

(56) References Cited

U.S. PATENT DOCUMENTS

| | | | |
|---|---|---|---|
| 2011/0042649 A1* | 2/2011 | Duvall | B82Y 10/00 257/27 |
| 2011/0315655 A1 | 12/2011 | Asano | |
| 2012/0261644 A1 | 10/2012 | Dimitrakopoulos | |
| 2012/0282594 A1 | 11/2012 | Chen et al. | |
| 2013/0000961 A1 | 1/2013 | Strachan et al. | |
| 2013/0157034 A1 | 6/2013 | Choi et al. | |
| 2014/0127896 A1 | 5/2014 | Bonilla et al. | |
| 2014/0220773 A1 | 8/2014 | Tour et al. | |
| 2015/0355540 A1* | 12/2015 | Shin | G03F 7/0047 430/18 |
| 2016/0187290 A1* | 6/2016 | Leburton | G01N 27/447 204/450 |

OTHER PUBLICATIONS

Gugang, C., et. al., "Sub-ppt gas detection with pristine graphene," Applied Physics Letters, vol. 101, 2012.

Gugang, C., et.al., "Enhanced gas sensing in pristine carbon nanotubes under continuous ultraviolet light illumination," Scientific Reports, vol. 2, (343), 2012.

Huang, B., et. al., "Adsorption of Gas Molecules on Graphene Nanoribbons and Its Implication for Nanoscale Molecule Sensor," Journal of Physical Chemistry, vol. 112, (35), pp. 13442-13446, 2008.

Jacobberger, R., et. al., "Direct oriented growth of armchair graphene nanoribbons on germanium," Nature Communications, vol. 6, 2015.

Kwon et. al., Developing ultrasensitive pressure sensor based on graphene nanoribbon: Molecular dynamics simulation. Physica E-Low-Dimensional Systems& Nanostructures, pp. 6-11, 47, 2013.

Li, Y. et. al., "MoS2 Nanoribbons: High Stability and Unusual Electronic and Magnetic Properties" Journal of the American Chemical Society, vol. 130, pp. 16739-16744, 2008.

Lin, Y.M., et. al., "Wafer-Scale Graphene Integrated Circuit", Science, vol. 332, pp. 1294-1297, 2011.

Mitoma, N., et. al., "Gate-controlled ultraviolet photo-etching or graphene edges," Applied Physics Letters, vol. 103, 2013.

Pak, Y., et. al., "Palladium-Decorated Hydrogen-Gas Sensors Using Periodically Aligned Graphene Nanoribbons," ACS Applied Materials & Interfaces, vol. 6, (15), pp. 13293-13298, 2014.

Ritter, C., et. al., "Graphene nanoribbon molecular sensor based on inelastic transport," Applied Physics Letters, vol. 104, (14), 2014.

Shao, L., et. al., "Suffer dioxide molecule sensors based on zigzag graphene nanoribbons with and without Cr dopant," Physics Letters A, vol. 378, (1) pp. 667-671, 2014.

Terrones, et. al., "Graphene and graphite nanoribbons: Morphology, properties, synthesis, defects and applications," Nano Today, pp. 351-372, 5, (4), 2010.

Yang, D., et. al. "UV/O3 Generated Graphene Nanomesh: Formation Mechanism, Properties, and FET Studies," The Journal of Physical Chemistry, vol. 118, (1), pp. 725-731, 2013.

* cited by examiner

CHEMICAL SENSOR BASED ON LAYERED NANORIBBONS

CLAIM OF PRIORITY UNDER 35 U.S.C. § 119

The present application for patent claims priority to Provisional Application No. 62/313,526, entitled "CHEMICAL SENSOR BASED ON LAYERED NANORIBBONS" filed Mar. 25, 2016, which is assigned to the assignee hereof and hereby expressly incorporated by reference herein for all purposes.

BACKGROUND

Increasing apprehension and concern for environmental and life forms evolution, industrial emissions, earlier medical diagnostics, and public and food safety, among other factors, have raised demand for higher level of sensitivity detection and monitoring of vital chemical and biological species in extremely low concentrations. Advances in nanostructured materials have enabled the emergence of a new generation of ultra-sensitive solid-state sensors having a high surface-to-volume ratio, high porosity, and exceptional chemical properties. Due to limitations in the structures and materials used in such sensors, however, the detection limit is typically in parts per million (PPM). As advances continue to be made in this technology, more focused detection limits may be desired.

SUMMARY

The following presents a summary of one or more aspects of the disclosure in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the disclosure in a simplified form as a prelude to the more detailed description that is presented later.

In an example, a chemical sensor is provided including a substrate comprising a plurality of nanoribbons of an active layered nanomaterial, and a substance detection component for measuring a change in electrical or physical properties of at least a portion of the plurality of nanoribbons when in contact with a substance.

In another example, a method for detecting substances using a chemical sensor is provided. The method includes supplying a charge to a plurality of layered nanoribbons positioned on a substrate, wherein the plurality of layered nanoribbons are composed of an active layered nanomaterial, monitoring changes in physical or electrical properties of the plurality of layered nanoribbons, and detecting presence of a substance based on determining that the changes in the physical or electrical properties of the plurality of layered nanoribbons achieve a threshold.

In yet another example, a method for constructing a substrate to facilitate chemical detection by a chemical sensor is provided. The method includes disposing an active layered nanomaterial over a substrate, coating the active layered nanomaterial with a photoresist layer, applying a mask, having a plurality of parallel beams, to the photoresist layer, developing the substrate to expose areas of the active layered nanomaterial covered by the mask to create a plurality of nanoribbons of the active layered nanomaterial coated with the photoresist layer, etching away the exposed areas of the active layered nanomaterial to achieve a substantially uniform edge configuration for edges of the plurality of nanoribbons, and removing a remaining portion of the photoresist layer from the plurality of nanoribbons To the accomplishment of the foregoing and related ends, one or more aspects of the disclosure comprise features hereinafter fully described and particularly pointed out in the claims. The following description and the annexed drawings set forth in detail certain illustrative features of the one or more aspects. These features are indicative, however, of but a few of the various ways in which the principles of various aspects can be employed, and this description is intended to include all such aspects and their equivalents.

BRIEF DESCRIPTION OF THE DRAWINGS

The novel features believed to be characteristic of aspects described herein are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The disclosure itself, however, as well as a preferred mode of use, further objects and advances thereof, will be best understood by reference to the following detailed description of illustrative embodiments when read in conjunction with the accompanying drawings, wherein:

DETAILED DESCRIPTION

The detailed description set forth below in connection with the appended drawings is intended as a description of various configurations and is not intended to represent the only configurations in which the concepts described herein can be practiced. The detailed description includes specific details for the purpose of providing a thorough understanding of various concepts. However, it will be apparent to those skilled in the art that these concepts can be practiced without these specific details. In some instances, well known structures and components are shown in block diagram form in order to avoid obscuring such concepts.

Figure 3:
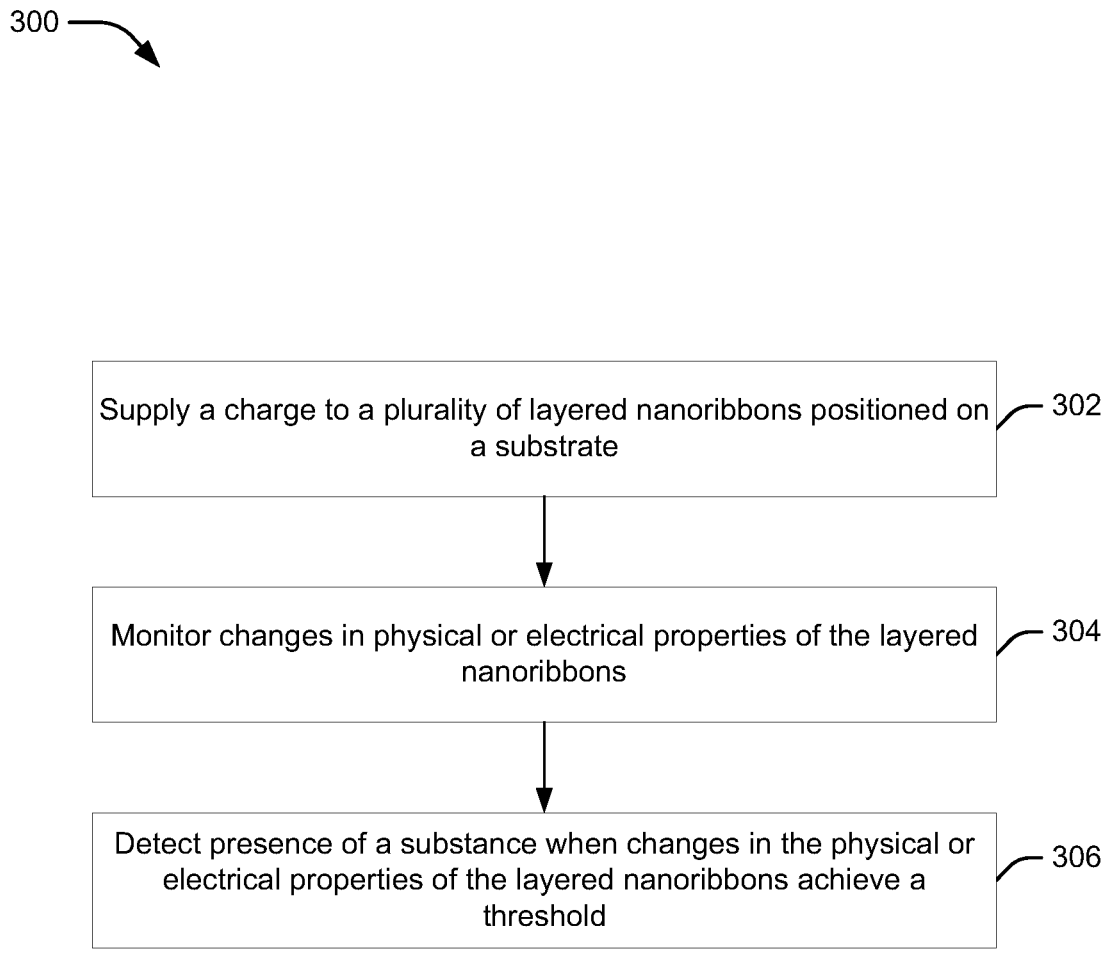
FIG. 3 illustrates a flowchart showing an example of a method for detecting changes in properties of a substrate according to one aspect of the disclosure.
Figure 5:
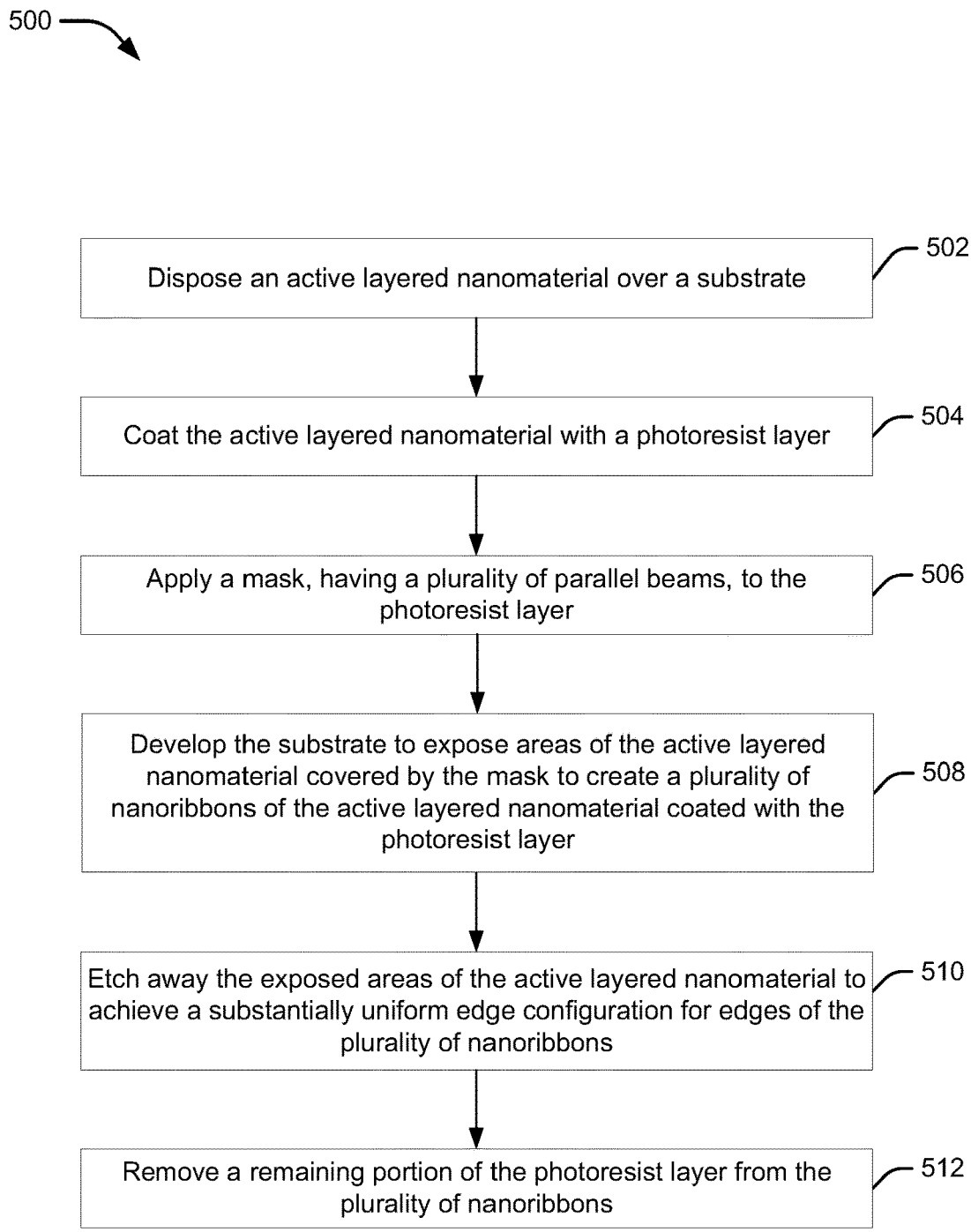
FIG. 5 illustrates a flowchart showing an example of a method for constructing nanoribbons according to one aspect of the disclosure.

Several aspects of certain systems will now be presented with reference to various apparatus and methods. These apparatus and methods will be described in the following detailed description and illustrated in the accompanying drawings by various blocks, modules, components, circuits, steps, processes, algorithms, etc. (collectively referred to as "elements"). These elements can be implemented using electronic hardware, computer software, or any combination thereof. Whether such elements are implemented as hardware or software depends upon the particular application and design constraints imposed on the overall system. Additionally, although the operations described below in various Figures, such as FIGS. 3 and 5, are presented in a particular order and/or as being performed by an example component, the ordering of the actions and the components performing the actions may be varied, in some examples, depending on the implementation.

Figure 1:
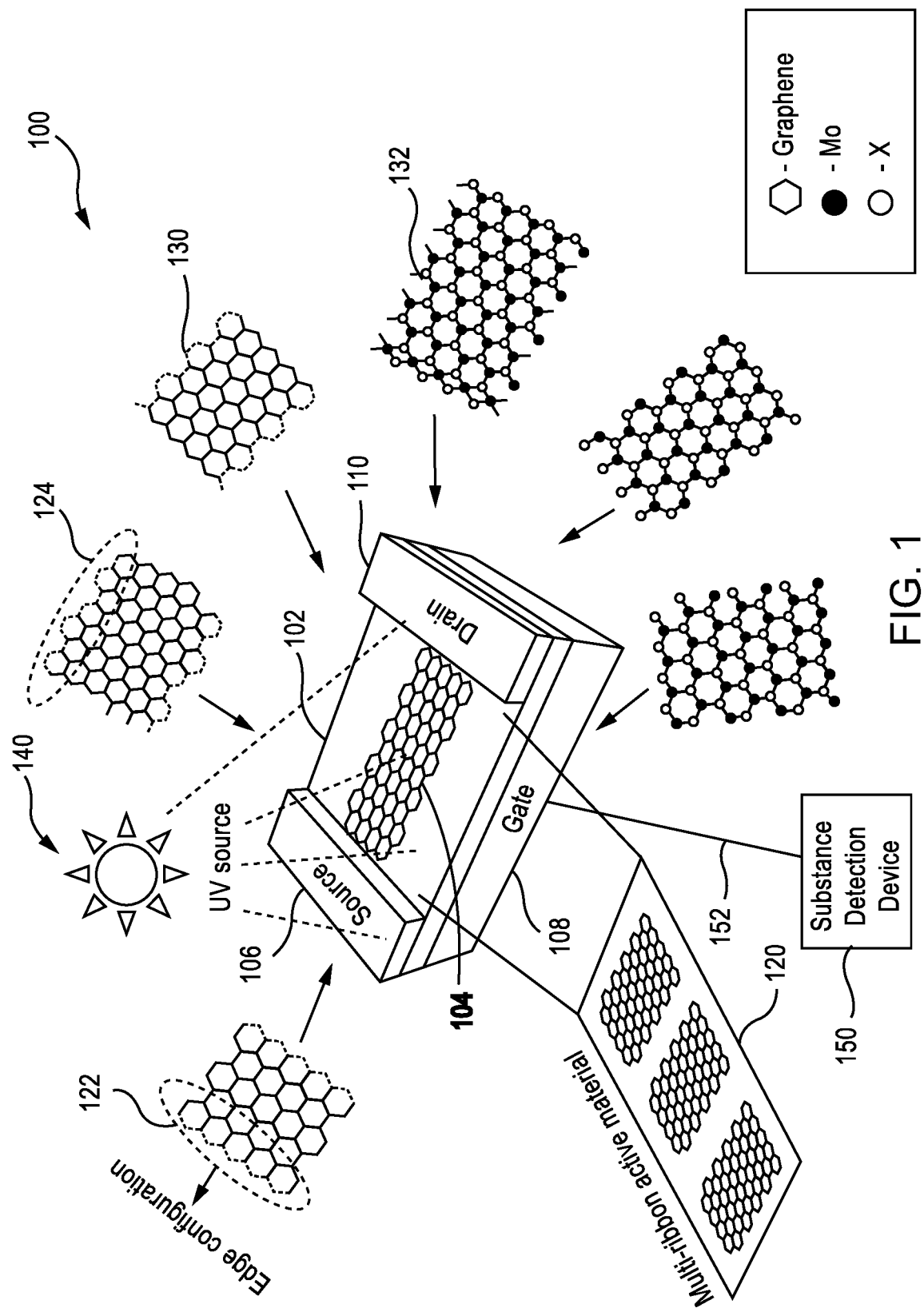
FIG. 1 illustrates a schematic view of an example of a sensor according to one aspect of the disclosure.

FIG. 1 shows an example chemical sensor 100 in accordance with aspects described herein. For example, sensor 100 can include a substrate 102 and a nanoribbon 104 of an active layered nanomaterial positioned thereon. Sensor 100 can also include components for introducing current through the nanoribbon to detect a reaction thereof in determining presence of a substance (e.g., a chemical substance, which may include a molecular analyte or similar substance), such as a source terminal 106, a gate terminal 108 for supplying a potential or charge to the source terminal 106, and a drain terminal 110 for receiving a current from the source terminal 106 based on the charge supplied to the source terminal 106. Thus, for example, sensor 100 may operate as or otherwise include a chemical field effect transistor (FET) to detect presence of a substance on or near the sensor 100 (e.g., on or near the nanoribbon 104) by detecting a change in electrical or physical property of the nanoribbon 104. In one example, sensor 100 can be coupled to a substance detection device 150 (e.g., via an electrical connection 152) that can detect presence of the substance based on monitoring and/or measuring changes in the electrical or physical properties of the nanoribbon 104.

The substrate 102 may comprise silica, alumina, MCM-41, MgO, ZrO2, aluminum-stabilized magnesium oxide, zeolites, or other supports known in the art, and combinations thereof. The nanoribbon 104 of the active layered nanomaterial may comprise graphene 130, 2-dimensional (2D) metal chalcogenides 132, such as sulfide materials (e.g., molybdenum disulfide ($MoS_2$) or similar materials), carbon nanotubes (CNT), black phosphorus, nitrides (e.g., hexagonal boron nitride), oxides (e.g., vanadium pentoxide), substantially any metal, and/or the like.

In an example, physical (e.g., transport) and/or electronic properties of the active layered nanomaterials of the nanoribbon 104, which may be measured to detect presence of a substance, may depend on a width of the ribbon and/or a configuration of atoms at the edges of the nanoribbon 104. In one example, the edges of the nanoribbon 104 may be more active than the planar region, and thus, in an example configuration, a plurality 120 of nanoribbons 104 may be provided on the substrate 102 to increase the number of edges, and thus the sensitivity of the sensor 100. In addition, providing the plurality of 120 of nanoribbons can increase the radio of edge to planar surface on the sensor 100 as compared to an infinite planar material or where the aspect ratio of nanoribbons is increased, which can additionally increase the sensitivity of the sensor 100. Moreover, for example, certain edge structures for the atoms may be more sensitive to certain classes of substances than others. Thus, for example, each nanoribbon 104 (or at least a portion of the plurality 120 of nanoribbons 104) may have an edge structure tailored to the class of substance to be detected by sensor 100. The edge structure may be substantially uniform along the edge, in an example, as shown and described herein. Moreover, in an example, the edges having the edge profile may be the edges that are configured substantially perpendicular to the source terminal 106 and the drain terminal 110 in the sensor 100 depicted in FIG. 1, though in some examples additional or alternative edges may have the edge profile. In addition, in an example, one or more of the plurality 120 of nanoribbons 104 may have a different edge profile than another one of the plurality 120 of nanoribbons 104. In yet another example, a nanoribbon 104 may have an edge profile on one side of the nanoribbon 104, and a different edge profile on another side of the nanoribbon 104.

Figure 2:
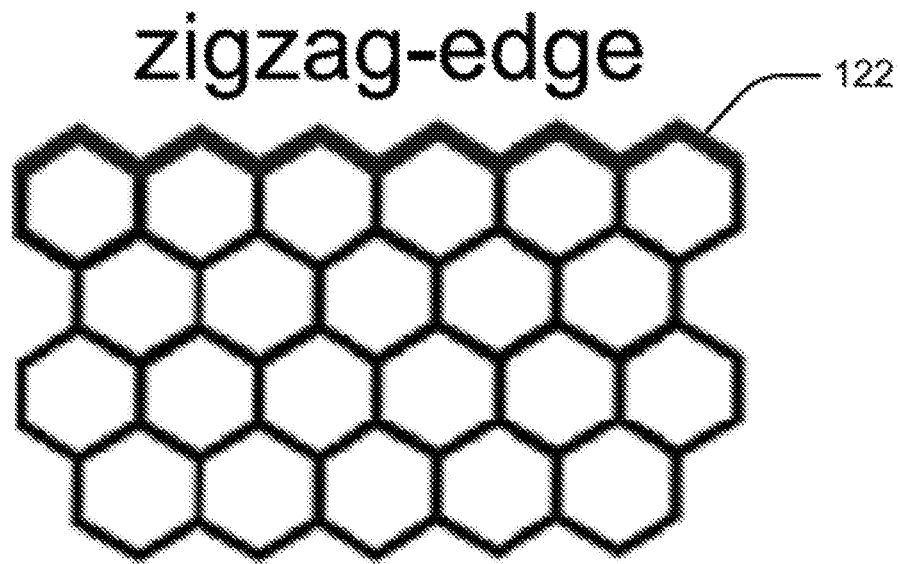
FIG. 2 illustrates examples of edge configurations of nanoribbons according to one aspect of the disclosure.
Figure 2:

In an example, as shown in FIG. 2, the edge profile may include a zigzag edge 122, an armchair edge 124, or substantially any edge profile. As shown, for example, the active layered nanomaterial can have a hexagonal shaped structure where edges are shared between atoms of the nanomaterial. Accordingly, for example, the atoms may be rotationally positioned on a substrate of the nanoribbon 104 such that the atoms on the edge of the nanoribbon 104 expose an edge angularly offset from an end of the nanoribbon 104, as with the zigzag edge 122. In another example, the atoms may be rotationally positioned on the substrate such that the atoms on the edge expose an edge that is substantially parallel with an end of the nanoribbon 104, as with armchair edge 124. In either case, during an etching process as described further with respect to FIGS. 4-5, the edges can be etched depending on the rotational position of the atoms to achieve a zigzag edge 122 or armchair edge 124 as a substantially uniform edge along an end of the nanoribbon 104.

Additionally, for example, nanoribbons 104 including the edges may deteriorate over time due to the current passing through the nanoribbons 104 and/or modification of the nanoribbons 104 when in the presence of the certain detectable substances. Exposing the nanoribbons 104 to ultraviolet (UV) light 140 can restore and clean the nanoribbons 104 and their edges. Thus, in an example, the nanoribbons 104 can be exposed to UV light 140 in situ to maintain and improve performance of the nanoribbons 104 in detecting substances. For example, the nanoribbons 104 may be exposed to UV light 140 in an optimal operating condition specifically to maintain/improve performance. For example, the nanoribbons 104 can be exposed to UV light 140 to facilitate purification through gas desorption, Plasmon resonance, electromagnetic field enhancement, thermal heating, direct photo-desorption, etc. Moreover, in an example, substance detection device 150 may determine whether changes in the nanoribbons 104 indicate presence of a substance and/or may take into account charge impurities that may be caused by the UV light 140, a photoelectrical effect, etc. Other methods to clean and restore nanoribbon performance may include thermal heating, other radiations, etc. For example, the nanoribbons 104 can be continuously exposed to a radiating light or radiation, such that the UV light 140 is continuously present for the heating the nanoribbons 104.

As described, the nanoribbons 104 may be composed of $MoS_2$, in one example, which may be more stable in environments that contain oxygen (e.g., in dry air under continuous UV light illumination) than other materials, such as graphene and CNT. In an example, the structure of the nanoribbons 104 may be selected in this regard (e.g., the material, number and spacing of nanoribbons, edge configuration, etc.) based on a substance to be detected by the corresponding sensor 100, an environment in which the sensor 100 is to be used, etc. In an example, a sensor 100 may include substantially any number of nanoribbons 104 to facilitate detection of certain materials. In an example, the number of nanoribbons 104 used may be based on the size of the sensor 100, the size of the nanoribbons 104, a space between the nanoribbons 104, etc. In one specific example, a 1 millimeter (mm) wide sensor 100 may include thousands of nanoribbons 104 (e.g., 10,000 to 100,000 nanoribbons 104). In a specific example, the 1 mm side sensor 100 may include around 33,000 nanoribbons 104 where the nanoribbons 104 are 15 nm wide and spaced with a 15 nanometer (nm) gap between nanoribbons.

Referring now to FIG. 3, an example method 300 for operating a sensor, such as sensor 100 (e.g., by substance detection device 150), is illustrated. In block 302, a charge can be supplied to a plurality of layered nanoribbons on a substrate. In an aspect, for example, substance detection device 150 can supply the charge to the nanoribbons 104 (e.g., source terminal 106) on the substrate 102. In an example, the source terminal 106 can supply the charge, and the drain terminal 110 can receive a current from the source terminal 106 that allows substance detection device 150 to monitor the physical/electrical changes in the nanoribbons 104 when a substance is near or in contact with the nanoribbons 104. Moreover, as described, the use of a plurality 120 of the nanoribbons 104 increases the number of edges, and thus the level of activity that can be detected by the substance detection device 150.

In block 304, changes in physical or electrical properties of the layered nanoribbons 104 may be monitored. In an aspect, substance detection device 150 can monitor the changes in physical or electrical properties of the nanoribbons 104, as described. For example, the changes may correspond to changes in the composition of the atoms on the nanoribbons 104 based on presence of a substance near or on the nanoribbons 104. The physical or electrical properties that may be monitored can be, for example and without limitation, the conductivity, dielectric constant, dielectric strength, permeability, permittivity, piezoelectric constant, Seebeck coefficient, thermopower, capacitance, wave impedance, wave absorption, emission, luminescence, luminance, thermal conductivity, mechanical and optical properties of the nanoribbons 104. By applying, for example, a voltage from the source terminal through the nanoribbons 104 (e.g., to the drain terminal) it can be possible to monitor the change in the electrical or physical property (e.g., changes to the current flowing between the source and drain terminals) caused in the nanoribbons 104 upon contact with a substance. One property can include a change in conductance of the nanoribbons 104, which can indicate presence of a substance near or on the nanoribbons 104. Additionally, as described, different configurations of edge profile of the edges of the nanoribbons 104 can exhibit different changes in composition based on presence of different substances.

In block 306, presence of a substance can be detected when changes in the physical or electrical properties of the layered nanoribbons achieve a threshold. In an aspect, substance detection device 150 can detect presence of the substance when changes in the physical or electrical properties of the nanoribbons 104 achieve a threshold. In one example, substance detection device 150 can determine the changes based on detecting electrical resistance over the nanoribbons 104 (e.g., based on changes in current received at the drain terminal 110), which may include detecting the resistance over one or more of the nanoribbons 104 by evaluating properties at the drain terminal 110, gate terminal 108, etc.

Figure 4:
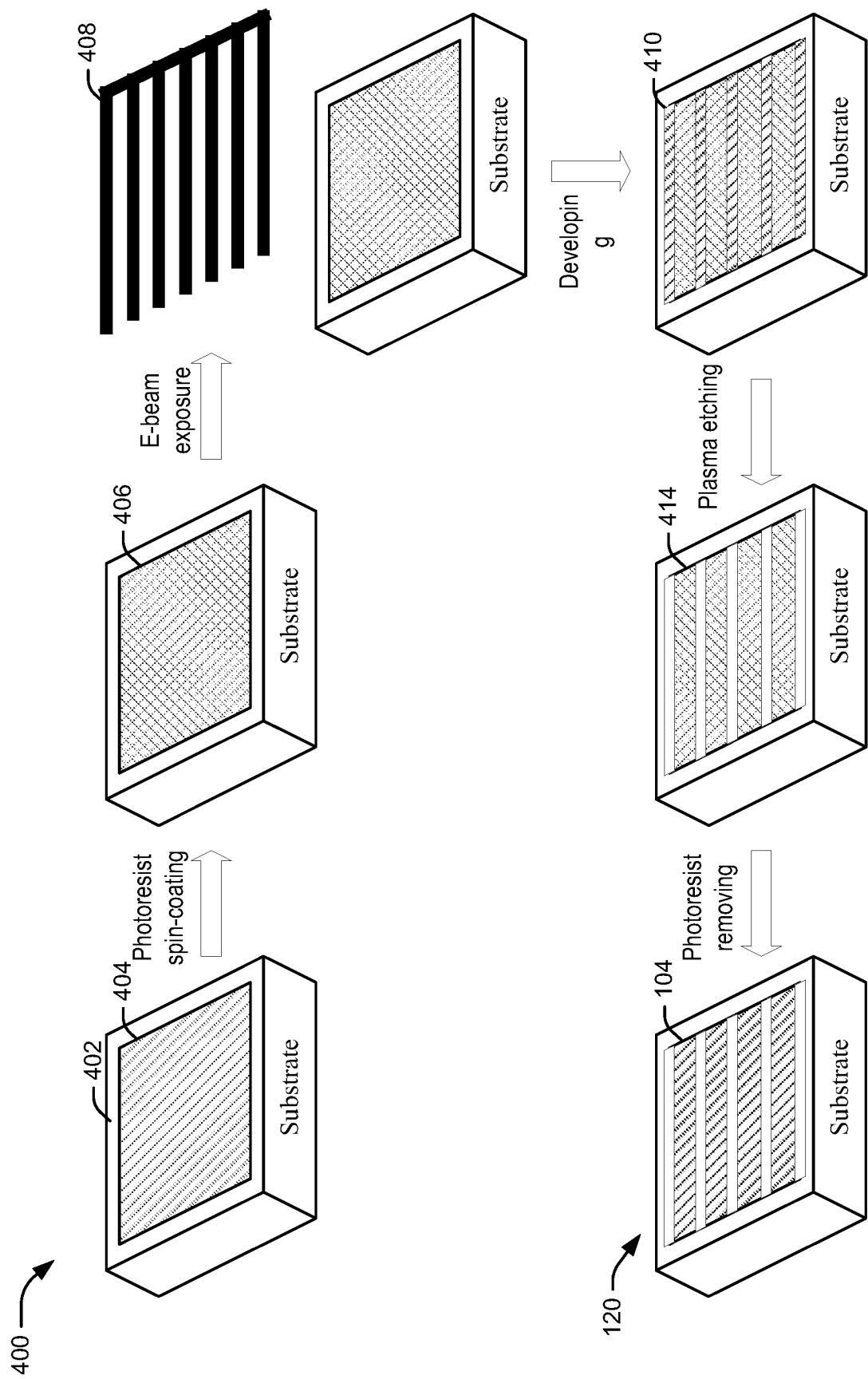
FIG. 4 illustrates an example of a process for constructing nanoribbons according to one aspect of the disclosure.

Referring to FIGS. 4 and 5, an example of a process and associated method for constructing nanoribbons described herein are illustrated. FIG. 4 illustrates an example of a process 400 for constructing the plurality 120 of nanoribbons 104, described above, using an industrial process, such as photolithography. FIG. 5 illustrates an example method 500 for performing the steps of the process 400.

In block 502, an active layered nanomaterial can be disposed on a substrate. For example, given a substrate 402, and active layered nanomaterial 404 can be disposed at least partially on the substrate 402. For example, the active layered nanomaterial 404 may include graphene 130, 2D metal chalcogenides 132, such as sulfide materials (e.g., molybdenum disulfide ($MoS_2$) or similar materials), carbon nanotubes (CNT), black phosphorus, nitrides (e.g., hexagonal boron nitride), oxides (e.g., vanadium pentoxide), substantially any metal, etc., as described above.

In block 504, the active layered nanomaterial can be coated with a photoresist layer. For example, the active layered nanomaterial 404 can be at least partially coated with a photoresist layer 406, which may be substantially any light-sensitive layer.

In block 506, a mask, having a plurality of parallel beams, can be applied to the photoresist layer. For example, the mask may be an E-beam mask 408 having the plurality of parallel beams, and may be composed of a material to optically resist light from passing through the beams.

In block 508, the substrate can be developed to expose areas of the active layered nanomaterial covered by the mask to create a plurality of nanoribbons of the active layered nanomaterial coated with the photoresist layer. For example, substrate 402, and the various layers, can be developed by exposing the substrate 402 to a light source. In one example, negative photoresist can be used for the photoresist layer 406 such that the non-exposed areas 410 of the photoresist layer 406 (e.g., the areas covered by the mask) may become soluble during developing.

In block 510, the exposed areas of the active layered nanomaterial can be etched away to achieve a substantially uniform edge configuration for edges of the plurality of nanoribbons. For example, the non-exposed areas 410 can be etched away using plasma etching, laser etching, etc. to yield a plurality of nanoribbons 414 of activate layered nanomaterial coated in material of the photoresist layer. In an example, the etching can be applied to achieve one or more edge profiles described herein, such as a zigzag edge 122, an armchair edge 124, etc. along the sides of each of the plurality of nanoribbons 414 coated in the photoresist layer material.

In block 512, a remaining portion of the photoresist layer can be removed from the plurality of nanoribbons. For example, the remaining portion of the photoresist layer on nanoribbons 414 can be removed to expose the plurality 120 of nanoribbons 104 of the active layered material, and having the substantially uniform edge configuration, as described above. For example, the remaining portion of the photoresist layer may be removed using a chemical stripper, an ashing process, etc. The substrate 402 with the plurality 120 of nanoribbons 104 can be used in a sensor 100, as described above, with a source terminal 106, gate terminal 108, and drain terminal 110 to detect one or more substances.

It will be appreciated that various implementations of the above-disclosed and other features and functions, or alternatives or varieties thereof, can be desirably combined into many other different systems or applications. Also that various presently unforeseen or unanticipated alternatives, modifications, variations, or improvements therein can be subsequently made by those skilled in the art which are also intended to be encompassed by the following claims.

What is claimed is:

1. A chemical sensor, comprising:
   a substrate comprising at least one layer having a planar surface;
   a plurality of nanoribbons of an active layered nanomaterial positioned on the layer of the planar surface of the substrate, wherein the plurality of nanoribbons have a substantially uniform edge configuration of a number of edges, and wherein the plurality of nanoribbons are configured as a plurality of parallel beams on the layer to increase a ratio of the number of edges to planar surface, wherein the ratio correlates to a sensitivity for the chemical sensor;

a source terminal for providing a charge to the plurality of nanoribbons;

a gate terminal for supplying the charge via the source terminal; and a drain terminal for receiving a current from the source terminal based on the charge, wherein a measured change in electrical or physical properties of at least a portion of the plurality of nanoribbons indicates presence of a substance.

2. The chemical sensor of claim 1, wherein the active layered nanomaterial includes graphene.

3. The chemical sensor of claim 1, wherein the active layered nanomaterial includes two-dimensional materials.

4. The chemical sensor of claim 3, wherein the two-dimensional materials include molybdenum disulfide.

5. The chemical sensor of claim 1, wherein the substantially uniform edge configuration includes one or more of a zigzag edge or an armchair edge.

6. The chemical sensor of claim 1, further comprising a radiation source for continuously radiating at least the portion of the plurality of nanoribbons to clean the active layered nanomaterial in at least the portion of the plurality of nanoribbons.

7. The chemical sensor of claim 6, wherein the radiation source supplies continuous ultraviolet light radiation.

8. The chemical sensor of claim 1, wherein the source terminal, the gate terminal, the drain terminal, and the substrate are part of a chemical field effect transistor (FET).

9. A method for detecting substances using a chemical sensor, comprising:

supplying a charge to a plurality of nanoribbons positioned on a layer of a planar surface of a substrate, wherein the plurality of nanoribbons are composed of an active layered nanomaterial, wherein the plurality of nanoribbons are configured as a plurality of parallel beams on the layer to increase a ratio of a number of edges of the plurality of nanoribbons to planar surface, wherein the ratio correlates to a sensitivity for the chemical sensor, and wherein the layer is one of one or more layers on the substrate;

monitoring changes in physical or electrical properties of the plurality of nanoribbons; and detecting presence of a substance based on determining that the changes in the physical or electrical properties of the plurality of nanoribbons achieve a threshold.

10. The method of claim 9, wherein the active layered nanomaterial includes graphene.

11. The method of claim 9, wherein the active layered nanomaterial includes two-dimensional materials.

12. The method of claim 11, wherein the two-dimensional materials include molybdenum disulfide.

13. The method of claim 9, wherein at least a portion of the plurality of nanoribbons have a substantially uniform edge configuration.

14. The method of claim 13, wherein the substantially uniform edge configuration includes one or more of a zigzag edge or an armchair edge.

15. A method for constructing a substrate to facilitate chemical detection by a chemical sensor, comprising:

disposing an active layered nanomaterial over a layer of a planar surface of the substrate;

coating the active layered nanomaterial with a photoresist layer;

applying a mask, having a plurality of parallel beams, to the photoresist layer;

developing the substrate to expose areas of the active layered nanomaterial covered by the mask to create a plurality of nanoribbons of the active layered nanomaterial coated with the photoresist layer on the layer of the planar surface of the substrate;

etching away the exposed areas of the active layered nanomaterial to achieve a substantially uniform edge configuration for a number of edges of the plurality of nanoribbons on the layer of the planar surface of the substrate to increase a ratio of the number of edges to planar surface, wherein the ratio correlates to a sensitivity for the chemical sensor; and removing a remaining portion of the photoresist layer from the plurality of nanoribbons to expose the plurality of nanoribbons as parallel nanoribbons on the layer of the planar surface.

16. The method of claim 15, wherein the active layered nanomaterial includes graphene.

17. The method of claim 15, wherein the active layered nanomaterial includes two-dimensional materials.

18. The method of claim 17, wherein the two-dimensional materials include molybdenum disulfide.

19. The method of claim 15, wherein the substantially uniform edge configuration includes one or more of a zigzag edge or an armchair edge.

* * * * *